United States Patent [19]

Boschelli et al.

[11] Patent Number: 5,114,958

[45] Date of Patent: May 19, 1992

[54] 1,2,4-OXADIAZOLE AND 1,2,4-THIADIAZOLE DERIVATIVES OF FENAMATES AS ANTIINFLAMMATORY AGENTS

[75] Inventors: Diane H. Boschelli, Plymouth; David T. Connor, Ann Arbor, both of Mich.

[73] Assignee: Warner-Lambert Company, Morris Plains, N.J.

[21] Appl. No.: 697,374

[22] Filed: May 9, 1991

[51] Int. Cl.$^5$ .................. A61K 31/41; C07D 271/06; C07D 285/08; C07D 285/14
[52] U.S. Cl. ................................. 514/361; 548/132; 548/133; 548/128; 548/129; 514/364
[58] Field of Search ............... 548/132, 133, 128, 129; 514/361, 364

[56] References Cited

FOREIGN PATENT DOCUMENTS 371438 6/1990 European Pat. Off. ............ 548/132

Primary Examiner—Patricia L. Morris
Assistant Examiner—Robert C. Whittenbaugh
Attorney, Agent, or Firm—Ronald A. Daignault

[57] ABSTRACT 1,2,4-Oxadiazole and 1,2,4-thiadiazole derivatives of the fenamic acids, in which the fenamate residue is present at the 3-position of the 1,2,4-oxadiazole or 1,2,4-thiadiazole, pharmaceutically acceptable acid addition or base salts and methods of preparation for such compounds as well as pharmaceutical compositions alone or in combination with a second active ingredient are described. The compounds are active as inhibitors of cyclooxygenase and/or 5-lipoxygenase thereby providing methods of treatment for antiinflammatory diseases.

13 Claims, No Drawings

1,2,4-OXADIAZOLE AND 1,2,4-THIADIAZOLE DERIVATIVES OF FENAMATES AS ANTIINFLAMMATORY AGENTS

BACKGROUND OF THE INVENTION

The present invention is directed to novel compounds which are 1,2,4-oxadiazole and 1,2,4-thiadiazole derivatives of the fenamic acids (in which the fenamate residue is present at the 3-position of the 1,2,4-oxadiazole or 1,2,4-thiadiazole), and pharmaceutically acceptable acid addition or base salts thereof, pharmaceutical compositions, and methods of use thereof. The invention compounds are found to have activity as inhibitors of cyclooxygenase and/or 5-lipoxygenase providing treatment of conditions advantageously affected by such inhibition including inflammation, arthritis, pain, fever, and the like.

Fenamates have been previously described as antiinflammatory agents and, particularly, various oxadiazole and thiadiazoles as useful substituents in derivations thereof. For example, 1,3,4-oxadiazole and 1,3,4-thiadiazoles are described in copending United States application Ser. No. 07/769/562. Certain 1,2,4-oxadiazole and 1,2,4-thiadiazoles are also described together with 3,5-di-tertiary-butyl-4-hydroxyphenyl groups in European Patent Publication 371,438. Nevertheless, the present combination of ring systems, substituents, and moieties is not among those previously known.

SUMMARY OF THE INVENTION

The present invention is a compound of formula I and pharmaceutically acceptable salts thereof

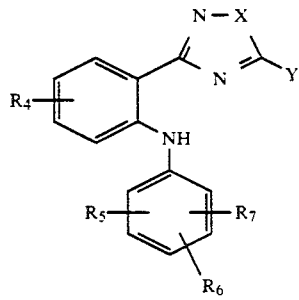

wherein
X is O or S;
Y is OH, SH, NH$_2$, OR$^1$, S(O)$_n$R$^1$, NR$^1{}_2$ or NHR$^2$, in which
  n is 0, 1, or 2;
  R$^1$ is lower alkyl or aryl,
  R$^2$ is lower alkyl, aryl, OR$^1$, CN, C(W)NHR$^3$, or NHC(W)NHR$^3$, in which
    R$^3$ is H, lower alkyl, phenyl, or substituted phenyl, and
    W is O, S, or NH; and
R$^4$, R$^5$, R$^6$, and R$^7$ are independently hydrogen, fluorine, chlorine, bromine, iodine, trifluoromethyl, lower alkyl, CN, hydroxy, lower alkoxy, S(O)$_n$-lower alkyl, NO$_2$, or NR$^8$R$^9$ wherein R$^8$ and R$^9$ are independently H, lower alkyl, or acyl.

The present invention also includes a pharmaceutical composition comprising an antiinflammatory effective amount of a compound of formula I in admixture with a pharmacologically acceptable carrier.

The present invention further includes a method of treating inflammation, arthritis, pain, or fever in a mammal suffering therefrom comprising administering to said mammal a pharmaceutical composition containing an active ingredient of an effective amount of a compound of formula I in unit dosage form.

DETAILED DESCRIPTION OF THE INVENTION

In compounds of formula I, the term "lower" preceding "alkyl" or "alkoxy" includes a hydrocarbon chain of from 1 to 6 carbon atoms such as ethyl, methyl, propyl, butyl, and the like or position isomers thereof.

The term "aryl" includes phenyl or substituted phenyl. Substituted phenyl is phenyl substituted by one to three substituents at the ortho, meta, and/or para positions, said substituents being independently fluorine, chlorine, bromine, iodine, trifluoromethyl, lower alkyl, CN, hydroxy, lower alkoxy, S(O)$_n$-lower alkyl, NO$_2$, or NR$^8$R$^9$ wherein R$^8$ and R$^9$ are independently H, lower alkyl, or acyl.

The term "acyl" is defined as a carboxylic acid derivative of the formula R-C(O) where R is lower alkyl or aryl as defined above. "Acyl" thus includes lower alkanoyl, benzoyl, or substituted benzoyl as defined above for substituted phenyl.

Compounds of formula I wherein Y is OH, SH, NH$_2$, or NHR$^2$ can exist as tautomers. These tautomers are represented as I and I'.

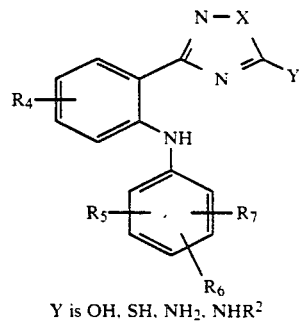

Y is OH, SH, NH$_2$, NHR$^2$

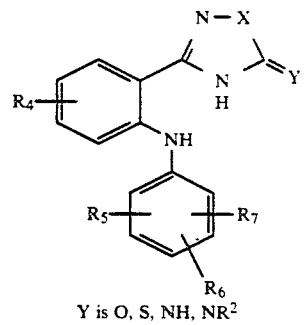

Y is O, S, NH, NR$^2$

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline; N-methylglucosamine; N-methylglucamine; L-glutamine; N-methylpiperazine; morpholine; ethylenediamine; N-benzylphenethylamine; tris(hydroxymethyl)-aminomethane; and the like. (See for example "Pharmaceutical Salts," *J. Pharm. Sci.*, 66(1):1-19 (1977).) Salts of inorganic bases include sodium, potassium, calcium, or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

A preferred embodiment of the present invention is a compound of formula I or a pharmaceutically acceptable salt thereof, wherein Y is OH, $S(O)_nR^1$ or $NHR^2$; $R_4$ is hydrogen, and $R_5$, $R_6$, and $R_7$ are each independently hydrogen, chlorine, trifluoromethyl, or lower alkyl.

A more preferred embodiment is a compound of formula I or a pharmaceutically acceptable salt thereof, wherein X is S; Y is $NHR^2$; $R_4$ is hydrogen, and $R_5$, $R_6$, and $R_7$ are each independently hydrogen, chlorine, or methyl.

A most preferred embodiment is a compound of formula I or a pharmaceutically acceptable salt thereof, wherein X is S; Y is $NHR^2$ in which $R^2$ is CN or $C(NH)NH_2$; $R_4$ is hydrogen, and $R_5$, $R_6$, and $R_7$ are each independently hydrogen, chlorine or methyl.

Particularly valuable are 3-[2-[(2,6-dichloro-3-methylphenyl)amino]phenyl]-1,2,4-thiadiazol-5-yl-guanidine or a pharmaceutically acceptable acid addition salt thereof, and 3-[2-[(2,6-dichloro-3-methylphenyl)amino]phenyl]-1,2,4-thiadiazol 5-yl-cyanamide.

A second aspect of preferred embodiments include a compound of formula I, wherein X is O and Y is OH.

More preferred is a compound of formula I, wherein X is O, Y is OH, $R_4$ is hydrogen, and $R_5$, $R_6$, and $R_7$ are each independently hydrogen, chlorine, or methyl.

Also, a particularly valuable compound of formula I, when X is O and Y is OH, is 3-[2-[(2,6-dichloro-3-methylphenyl)amino]phenyl]-1,2,4-oxadiazol-5(4H)one.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder of disease concerned. A suitable dose of a compound of formula I or pharmacologically acceptable salt thereof for a mammal suffering from, or likely to suffer from any condition as described hereinbefore is 0.1 μg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 μg of the compound per kilogram, typically about 0.1 μg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole cell 5-lipoxygenase and Cyclooxygenase Aasays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2\times10^6$ cells/mL. Cells are incubated with and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at −20° C. Aliquots (100 μL) are analyzed for $LTB_4$ and $PGF_{2\alpha}$ using radioimmunoassay kits as provided by the supplier.

Carrageenan-Induced Rat Foot Paw Edema-2 (CFE-2) Assay:Protocol

Carrageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40% inhibition occurs.

Table 1 contains biochemical data obtained from this whole cell assay as $IC_5s$ which are calculated as the amount of test compound causing 50% inhibition of $LTB_4$ or $PGF_{2\alpha}$ formation and the results of the CFE-2 assay.

TABLE 1

| Example | R | X | Y | ARBL[1] | ARBC[2] | CFE[3] |
|---|---|---|---|---|---|---|
| 2 | 2,6-diCl, 3-Me | S | $SO_2C_6H_4Me$ | N[4] | N | |
| 3 | 2,6-diCl, 3-Me | S | $NHC(NH)NH_2$ | 100% | N | |
| 4 | 2,6-diCl, 3-Me | S | NHCN | 6.15 | 1.23 | |
| 1 | 2,6-diCl, 3-Me | O | OH | 2.3 | .013 | 58% |

[1]$IC_{50}$ or % inhibition of $LTB_4$ at 10 μM
[2]$IC_{50}$ or % inhibition of $PGF_{2\alpha}$ at 10 μM
[3]Percent inhibition at 30 mg/kg
[4]N = Less than 40% inhibition at 10 μM In addition to the compounds of formula I, the pharmaceutical compositions can also contain other active ingredients such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:

(1) the propionic acid derivatives;
(2) the acetic acid derivatives;
(3) the fenamic acid derivatives;
(4) the biphenylcarboxylic acid derivatives; and
(%) the oxicams
or a pharmaceutically acceptable salt thereof.

The propionic acid derivatives which may be used comprise: ibuprofen, ibuprufen aluminum, indiprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$NA$^+$or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

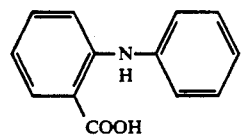

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

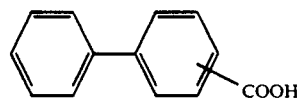

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam, and 4-hydroxyl-1,2-benzothiazine 1,1-dioxide 4 (N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

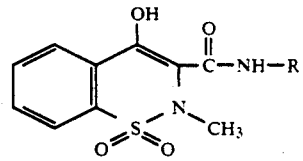

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α- fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

For example, the preparation of substituted 1,2,4-thiadiazoles is well known in the art (see *Advances in Heterocyclic Chemistry*, 32, 285 (1982), *Comprehensive Heterocyclic Chemistry*, 6, 463 (1984), and *Comprehensive Organic Chemistry*, 4, 1037 (1979)). Some specific methods are depicted in Scheme 1.

DESCRIPTION OF SCHEME 1

The nitrile analogs of the fenamates, compounds of type 1, are prepared according to the method of Juby, *J. Med. Chem.*, 11, 111 (1968). Reaction of compounds of type 1 with hydroxylamine hydrochloride in the presence of a base, preferably sodium methoxide in an alcoholic solvent such as methanol, provides amide oximes of formula 2. Treatment of compounds of type 2 with carbon disulfide provides compounds of formula 3 (see *Chem. Abs.*, 69, 86,998r). Reaction of compounds of type 3 with an alkyl or aryl halide in the presence of an inorganic base in a solvent such as THF or DMF or preferably in the presence of an organic base such as triethylamine in an alcoholic solvent, preferably methanol, yields compounds of formula 4. Treatment of compounds of type 2 with an alkyl or aryl isothiocyanate provides compounds of formula 5.

Reaction of amidines of formula 6 with dithiocyanogen leads to compounds of type 7 (for reference see *Chem. Ber.*, 87, 57 (1954)). These 5-amino-1,2,4-thiadiazoles are key intermediates in the preparation of additional compounds (see Scheme 4). Another key intermediate, compound 8, is obtained from amidine 6 via reaction with perchloromethylmercaptan (for reference see *Chem. Ber.*, 90, 1982 (1957)). Compounds of formula 8 can also be obtained by standard diazotization reactions on compounds of formula 7.

Starting with an amide of formula 9, prepared according to the method of Juby, *J. Med. Chem.*, 11, 111 (1968), reaction with chlorocarbonylsulfenyl chloride provides intermediate 1,3,4-oxathiazole of formula 10 (for reference see *J. Org. Chem.*, 42, 1813 (1977)). Treatment of 10 with an aryl or alkylsulfonyl cyanide, preferably p-toluenesulfonyl cyanide, in a solvent such as dichlorobenzene at elevated temperatures provides compounds of formula 11. Compounds of formula 8 and 11 are important intermediates in the preparation of additional compounds (see Scheme 3).

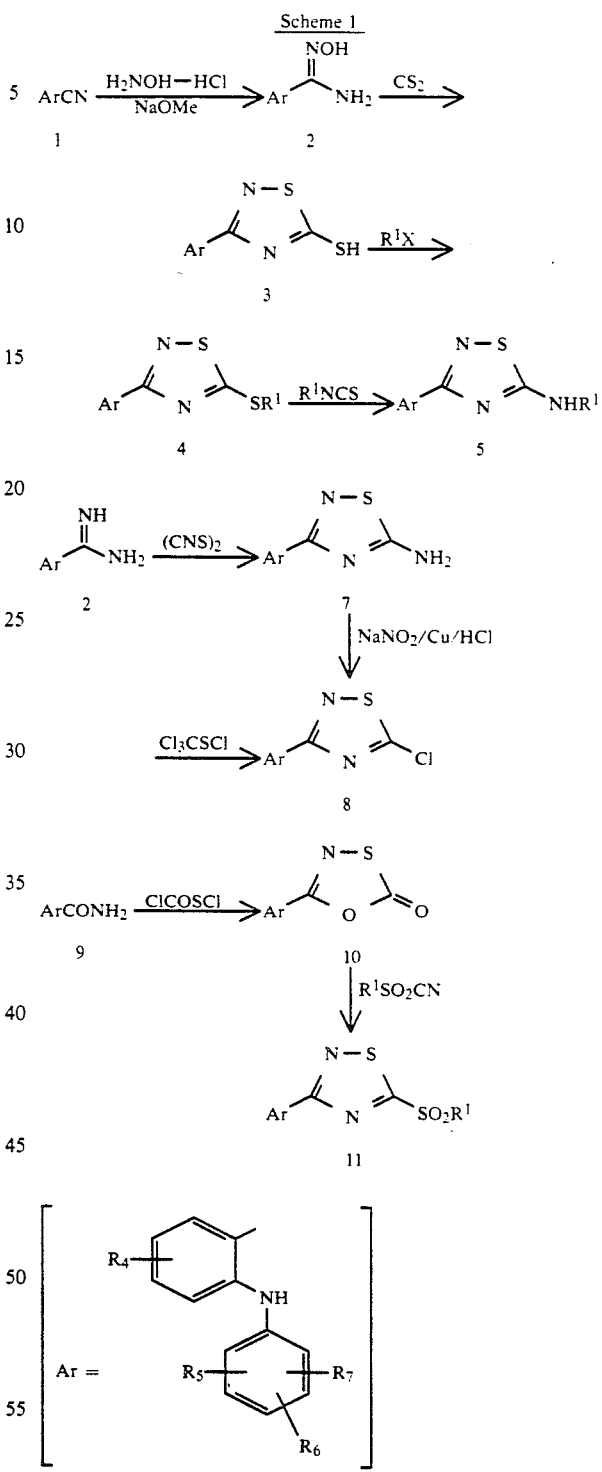

The preparation of substituted 1,2,4-oxadiazoles is also well known in the art (see *Advances in Heterocyclic Chemistry*, 20, 65 (1976), *Comprehensive Heterocyclic Chemistry*, 6, 365 (1984), and *Comprehensive Organic Chemistry*, 4, 1037–1041 (1979)). Some specific methods are depicted in Scheme 2.

DESCRIPTION OF SCHEME 2

Treatment of an amide oxime of formula 1 with ethyl chloroformate in the presence of an organic base, preferably triethyl amine, in a solvent such as methylene chloride, provides intermediates of formula 2. Heating compounds of formula 2 at reflux in a high boiling solvent such as toluene provides compounds of formula 3. These compounds can also be obtained directly from 1 by treatment with ethyl chloroformate in a basic solvent such as pyridine and heating at reflux (for reference see *Tetrahedron*, 21, 1681 (1965)). Reaction of amide oximes of formula 1 with carbon disulfide in the presence of a base such as sodium hydroxide in a suitable solvent such as methanol provides compounds of formula 4. Reaction of compounds of type 4 with an alkyl or aryl halide in the presence of an inorganic base in a solvent such as THF or DMF or preferably in the presence of an organic base such as triethylamine in an alcoholic solvent, preferably methanol, yields compounds of formula 5.

Compounds of formula 6 are key intermediates in the preparation of additional compounds (see Scheme 3). They are prepared by the method described in *Hel. Chim. Acta*, 46, 1067 (1963). Compounds of formula 8 are prepared via treatment of carboxyimidoyl halides of formula 7 with guanidine (see *Hel. Chim. Acta*, 49, 1430 (1966)). Once again the corresponding 5-chloro compounds of formula 9 can be obtained by standard diazotization reactions on the 5-amino group of compounds of formula 8.

additional compounds. These reactions are depicted in Scheme 3.

DESCRIPTION OF SCHEME 3

Compounds of type 2 are prepared by treating compounds of type 1 with the sodium or potassium salt of the corresponding thiol in aqueous DMF. Reaction of sulfides of formula 2 with sodium thiomethoxide leads to compounds of formula 3. Oxidation of compounds of type 2 with one equivalent of an oxidizing agent, such as hydrogen peroxide or an organic peracid, preferably m-chloroperbenzoic acid, in a solvent such as methylene chloride provides sulfoxides of formula 4. Use of two equivalents of oxidizing agent provides sulfones of formula 5.

Compounds of formula 6 are obtained by reaction of compounds of formula 1 with the corresponding sodium or potassium salt of the required alcohol in aqueous DMF as the preferred solvent. Treatment of compounds of formula 1 with aqueous acid or base provides compounds of formula 7.

The remainder of the compounds shown in Scheme 3 (9-13) are obtained by reaction of 1 with the corresponding nucleophile in a solvent such as ethanol, isopropanol, t-butanol, or aqueous DMF, in the presence or absence of a base. If aqueous DMF is used as the

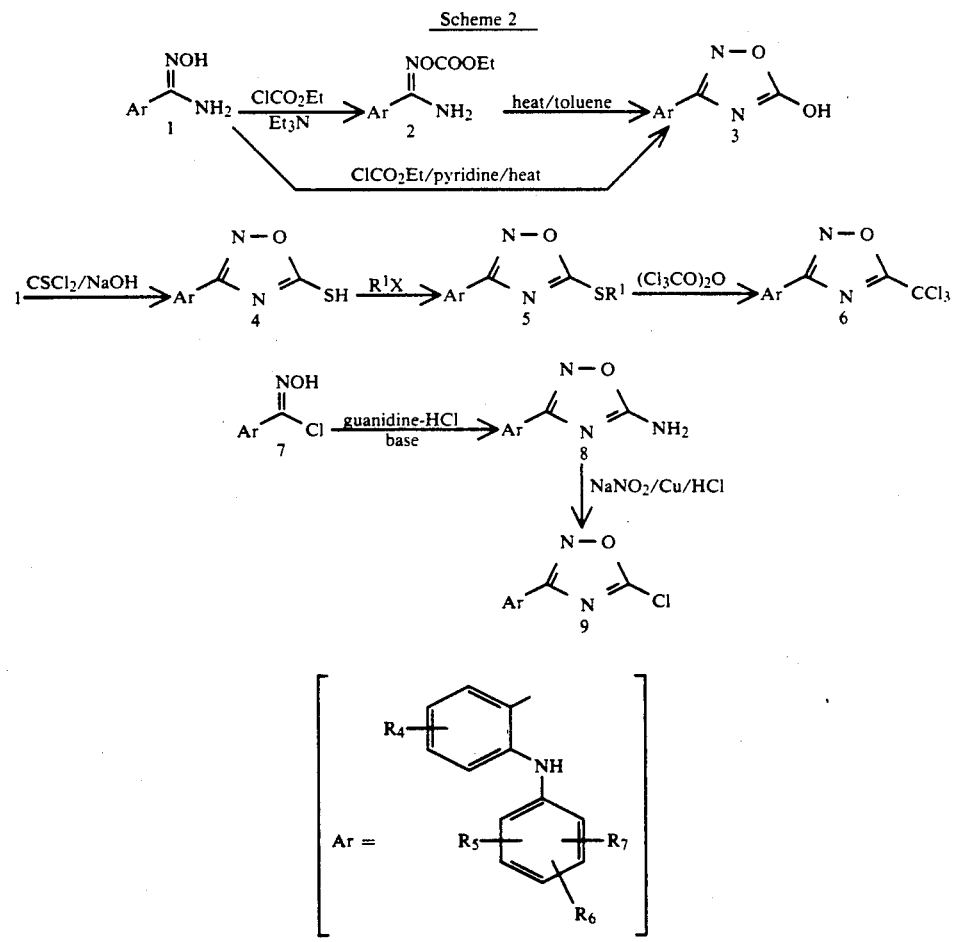

As stated, 1,2,4-thiadiazoles or 1,2,4-oxadiazoles having at position 5 a group such as chloro, trichloromethyl, or alkylsulfonyl that can easily be displaced by nucleophiles are intermediates in the preparation of solvent, the preferred base is triethyl amine. If alcohols are used as the solvent, the preferred base is potassium t-butoxide.

Scheme 3
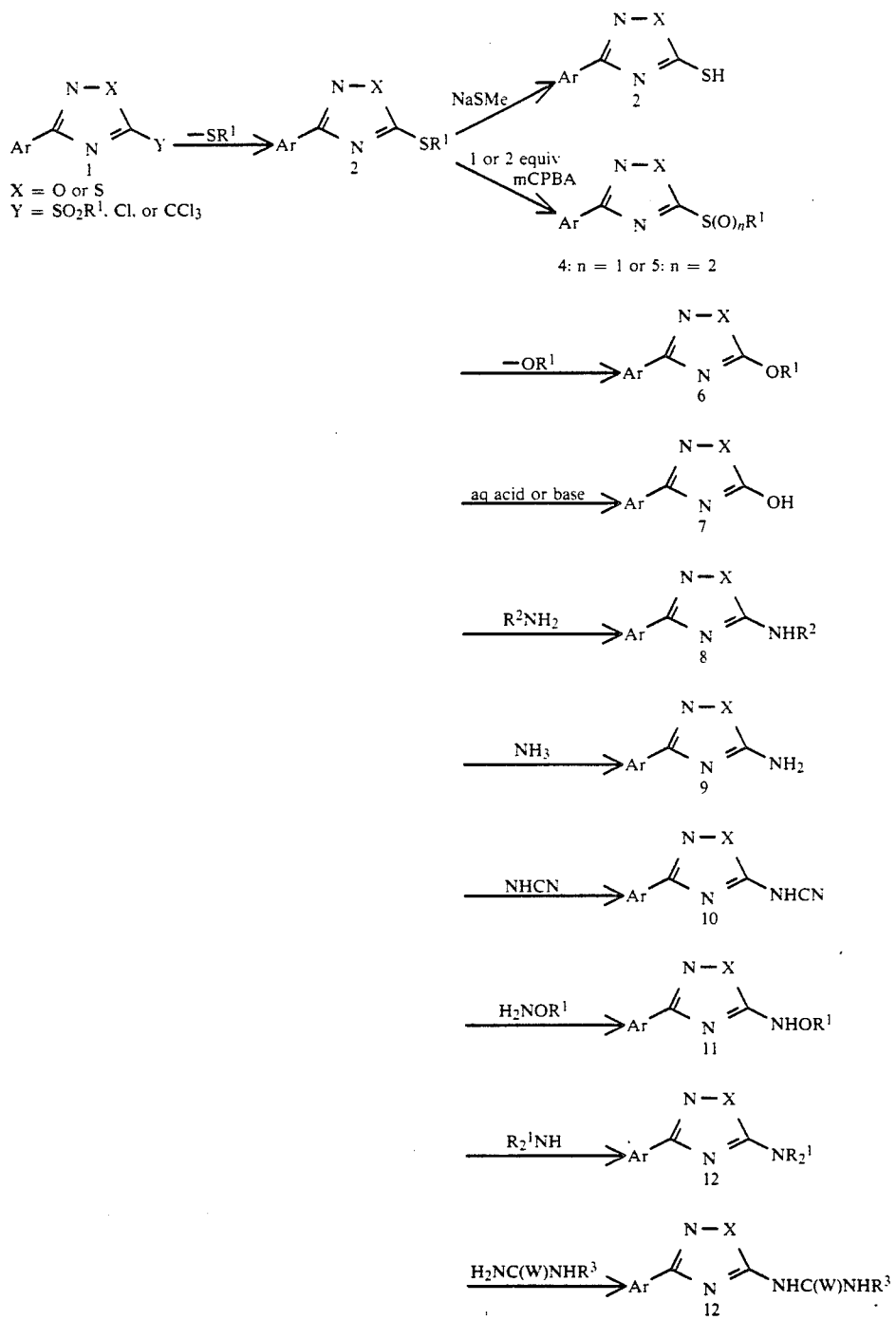
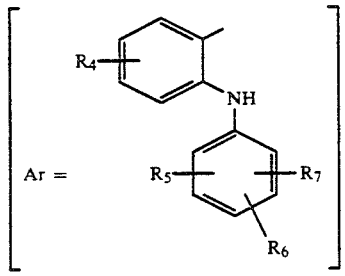

1,2,4-Thiadiazoles or 1,2,4-oxadiazoles with an amino group at position 5 can be used to prepare additional analogs as shown in Scheme 4.

DESCRIPTION OF SCHEME 4

Scheme 4 depicts the treatment of compounds of formula 1 with various isocyanates or isothiocyanates in solvents such as hexane, benzene, or toluene to provide compounds of formulas 2 to 5.

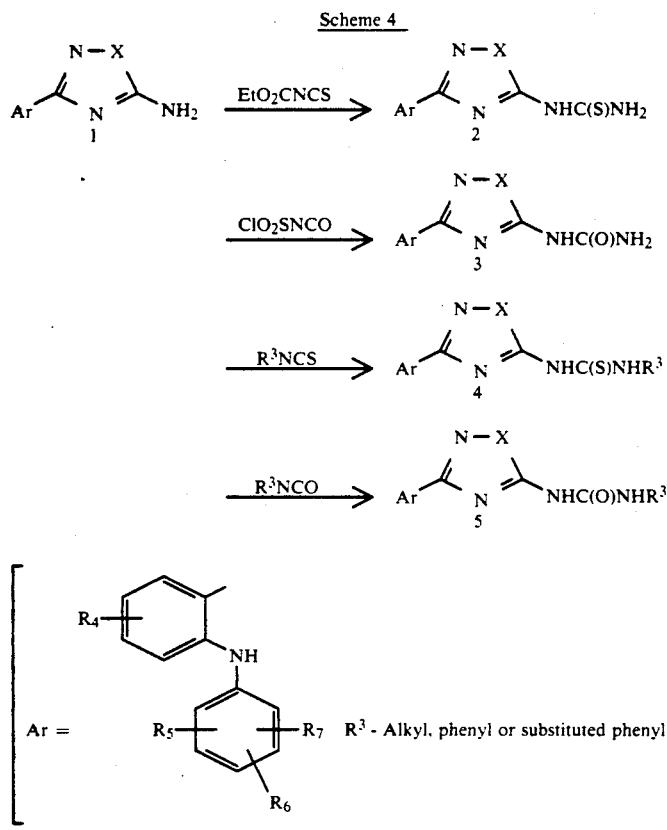

One of skill in the art would recognize variations in the sequence and would recognize variations in the appropriate reaction conditions from the analogous reactions shown or otherwise known which may be appropriately used in the processes above to make the compounds of the formula I herein. Further, starting materials are known or can be prepared by known methods.

The products of the reactions described herein are isolated by conventional means such as extraction, distillation, chromatography, and the like.

The invention is further illustrated by the representative examples as follows.

EXAMPLE 1

3-[2-[(2,6-Dichloro-3-methylphenyl)amino]phenyl]-1,2,4-oxadiazol-5(4H)-one (a) 2-(2,6-Dichloro-3-methylanilino)benzamide oxime To a room temperature solution of hydroxylamine hydrochloride (1.362 g, 19.62 mmols) in 40 mL of methanol is added sodium methoxide (1.030 g, 19.06 mmols). The mixture is stirred at room temperature for 15 minutes, then filtered. The filtrate is added to a suspension of 2-(2,6-dichloro-3-methylanilino)benzonitrile (3.109 g, 11.20 mmols) [prepared according to Juby, *J. Med. Chem.*, 11, 111 (1968)] in 70 mL of methanol and the mixture is heated at reflux overnight. The clear yellow solution is cooled and concentrated in vacuo. Flash chromatography eluting with 6:1 hexane: ethyl acetate provides 2.079 g (60%) of 2-(2,6-dichloro-3-methylanilino)benzamide oxime as a white solid.

(b) 3-[2-(2,6-Dichloro-3-methylphenyl)amino]phenyl]-1,2,4-oxadiazol-5(4H)-one

To a room temperature solution of 2-(2,6-dichloro-3-methylanilino)benzamide oxime (585 mg, 1.89 mmols) in 5 mL of pyridine is added ethyl chloroformate (250 μL, 2.62 mmols). The solution is heated at reflux for 1 hour, cooled, and concentrated in vacuo. Flash chromatography eluting with 2:1 hexane: ethyl acetate provides 295 mg (47%) of 3-[2-[(2,6-dichloro-3-methylphenyl)amino]phenyl]-1,2,4-oxadiazol-5(4H)-one as a white solid;

mp 209°-210° C.

Calc'd for $C_{15}H_{11}Cl_2N_3O_2$: C, 53.59; H, 3.30; Cl, 21.09; N, 12.50. Found: C, 53.47; H, 3.04; Cl, 21.27; N, 12.41.

(c) Sodium salt of 3-[2-[(2,6-dichloro-3-methylphenyl)amino]phenyl]-1,2,4-oxadiazol-5(4H)-one To a room temperature suspension of 3-[2-[(2,6-dichloro-3-methylphenyl)amino]phenyl]-1,2,4-oxadiazol-5(4H)-one (171 mg, 0.50 mmols) in 5 mL of methanol is added 1 N aqueous sodium hydroxide (500 μL, 0.50 mmols). The pale yellow solution is stirred at room temperature for 1.5 hours, then concentrated in vacuo and dried to constant weight, providing 181 mg (99%) of the sodium salt of 3-[2-[(2,6-dichloro-3- methylphenyl)amino]phenyl]-1,2,4-oxadiazol-5(4H)-one as a white solid; mp is undefined.

Calc'd for $C_{15}H_{10}Cl_2N_3O_2Na \cdot H_2O$: C, 47.89; H, 3.22; N, 11.17. Found: C, 47.51; H, 3.31; N, 11.08.

EXAMPLE 2

2,6-Dichloro-3-methyl-N-[2-[5-[(4-methylphenyl)-sulfonyl]-1,2,4-thiadiazol-3-yl]phenyl]benzenamine (a) 5-[2-[(2,6-Dichloro-3-methylphenyl)amino]-phenyl]-1,3,4-oxathiazol-2-one To a 90° C. solution of 2-(2,6-dichloro-3-methylanilino)benzamide (2.300 g, 7.79 mmols) [prepared according to Juby, J. Med. Chem., 11, 111 (1968)] in 40 mL of toluene is added chlorocarbonylsulfenyl chloride (1.300 mL, 15.38 mmols). Heating is continued at 90° C. for 1 hour. The solution is concentrated in vacuo and purified by flash chromatography, eluting with 10:1 hexane:diethyl ether providing 280 mg (10%) of 5-[2-[(2,6-dichloro-3-methylphenyl)amino]phenyl]-1,3,4-oxathiazol-2-one as a white solid; mp 135°–137° C.

Calc'd for $C_{15}H_{10}Cl_2N_2O_2S$: C, 51.00; H, 2.85; Cl, 20.08; N, 7.93. Found: C, 50.95; H, 2.59; Cl, 20.00; N, 7.90.

(b) 2,6-Dichloro-3-methyl-N-[2-[5-[(4-methylphenyl)-sulfonyl]-1,2,4-thiadiazol-3-yl]-benzenamine To a 155° C. solution of p-toluenesulfonyl cyanide (420 mg, 2.32 mmols) in 5 mL of m-dichlorobenzene is added 5-[2 [(2,6-dichloro-3-methylphenyl)amino]-phenyl]-1,3,4-oxathiazol-2-one (442 mg, 1.25 mmols) in three portions. Heating is continued for 1.5 hours. The solution is cooled to room temperature and directly purified by flash chromatography, eluting with 10:1 hexane:diethyl ether providing 446 mg (73%) of 2,6-dichloro-3-methyl-N-[2-[5-[(4-methylphenyl)sulfonyl]-1,2,4-thiadiazol-3-yl]phenyl]benzenamide as a bright yellow solid; mp 130.5°–135° C.

Calc'd for $C_{22}H_{17}Cl_2N_3O_2S_2$: C, 53.88; H, 3.50; N, 8.57; S, 13.07. Found: C, 54.09; H, 3.51; N, 8.40; S, 12.93.

EXAMPLE 3

3-[2-[(2,6-Dichloro-3-methylphenyl)amino]phenyl]-1,2,4-thiadiazol-5-yl-quanidine, monohydrochloride A suspension of guanidine hydrochloride (197 mg, 2.06 mmols) and potassium t-butoxide (150 mg, 1.33 mmols) in 10 mL of t-butanol is heated to 40° C. 2,6-Dichloro-3-methyl-N-[2-[5-[(4-methylphenyl)-sulfonyl]-1,2,4-thiadiazol-3-yl]phenyl]benzenamine (200 mg, 0.41 mmols), prepared as described in Example 2, is added and heating is continued at 55° C. for 10 minutes. The solution is cooled to room temperature, poured into ether, and washed with water followed by brine. The organic layer is dried over magnesium sulfate, filtered, and concentrated to 10 mL. A few drops of methanol saturated with HCl are added. The resultant precipitate is collected by filtration, providing 84 mg (48%) of 3-[2-[2,6-dichloro-3-methylphenyl)amino]phenyl]-1,2,4-thiadiazol-5-yl guanidine, monohydrochloride as a white solid; mp 268°–277° C.

Calc'd for $C_{16}H_{14}Cl_2N_6S \cdot HCl$: C, 44.71; H, 3.52; N, 19.56. Found: C, 44.40; H, 3.46; N, 19.53.

EXAMPLE 4

3-[2-[(2,6-Dichloro-3-methylphenyl)amino]phenyl]-1,2,4-thiadiazol-5-yl-cyanamide To a solution of cyanamide (124 mg, 2.96 mmols) in 5 mL of dimethylformamide is added triethylamine (150 μL, 1.08 mmols) followed by 2,6-dichloro-3-methyl-N-[2-[5-[(4-methylphenyl)sulfonyl]-1,2,4 -thiadiazol-3-yl]phenyl]benzenamine (176 mg, 0.36 mmols), prepared as described in Example 2. The mixture is heated at 75° C. for 4.5 hours. Additional cyanamide (82 mg) is added and heating is continued for 1.5 hours. The solution is cooled to room temperature and partitioned between ethyl acetate and 0.2 N aqueous sodium hydroxide. The layers are separated and an equal volume of hexane is added to the ethyl acetate layer which is then extracted with 1 N sodium hydroxide. The basic layers are combined and acidified with 10% aqueous hydrochloric acid. The resultant precipitate is collected by filtration, providing 106 mg (79%) of 3-[2-[2,6-dichloro-3-methylphenyl)amino]phenyl]-1,2,4-thiadiazol-5-yl -cyanamide as a light tan solid. An analytical sample was obtained by drying at 70° C. for 2 days, mp is undefined.

Calc'd for $C_{16}H_{11}Cl_2N_5S$: C, 51.07; H, 2.95; N, 18.61. Found: C, 50.97; H, 2.69; N, 18.92.

We claim:

1. A compound of the formula

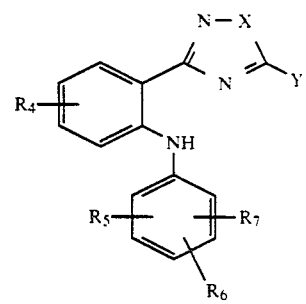

or a pharmaceutically acceptable salt thereof, wherein,

X is O or S;

Y is OH, SH, $NH_2$, $OR^1$, $S(O)_nR^1$, $NR^1_2$ or $NHR^2$, in which n is 0, 1, or 2; $R^1$ is lower alkyl, phenyl, or phenyl substituted by one to three substituents selected from fluorine, chlorine, bromine, iodine, trifluoromethyl, lower alkyl, CN, hydroxy, lower alkoxy, $S(O)_n$-lower alkyl, $NO_2$ and $NR^8R^9$ wherein $R^8$ and $R^9$ are independently hydrogen, lower alkyl, lower alkanoyl, benzoyl, or benzoyl substituted by one to three substituents selected from fluorine, chlorine, bromine, iodine, trifluoromethyl, lower alkyl, CN, hydroxy, lower alkoxy, $S(O)_n$-lower alkyl, $NO_2$, and $NR^{10}R^{11}$ wherein $R^{10}$ and $R^{11}$ are independently hydrogen or lower alkyl, and $R^2$ is lower alkyl, phenyl, or substituted phenyl as defined above, $OR^1$, CN, $C(W)NHR^3$ or $NHC(W)NHR^3$ wherein $R^3$ is hydrogen, lower alkyl, phenyl, or substituted phenyl as defined above, and W is O, S or NH; and $R^4$, $R^5$, $R^6$, and $R^7$ are each independently hydrogen, fluorine, chlorine, bromine, iodine, trifluoromethyl, lower alkyl, CN, hydroxy, lower alkoxy, $S(O)_n$-lower alkyl, $NO_2$, or $NR^8R^9$ wherein $R^8$ or $R^9$ are independently hydrogen, lower alkyl, lower alkanoyl, benzoyl, or substituted benzoyl as defined above.

2. A compound as claimed in claim 1, wherein Y is OH, $S(O)_nR^1$ or $NHR^2$; $R_4$ is hydrogen, and $R_5$, $R_6$, and $R_7$ are each independently hydrogen, chlorine, trifluoromethyl, or lower alkyl.

3. A compound as claimed in claim 2, wherein X is S; Y is $NHR^2$.

4. A compound as claimed in claim 3, wherein $R_5$, $R_6$, and $R_7$ are each independently hydrogen, chlorine, or methyl.

5. A compound as claimed in claim 4, wherein Y is $NHR^2$ in which $R^2$ is CN or $C(NH)NH_2$.

6. A compound as claimed in claim 5 and being 3-[2-[(2,6-dichloro-3-methylphenyl)amino]phenyl]-1,2,4-thiadiazol-5-yl-guanidine or a pharmaceutically acceptable acid addition salt thereof.

7. The compound of claim 6 as a monohydrochloride salt.

8. A compound as claimed in claim 5 and being 3-[2-[(2,6-dichloro-3-methylphenyl)amino]phenyl]-1,2,4,-thiadiazol-5-yl-cyanamide.

9. A compound as claimed in claim 2, wherein X is O and Y is OH.

10. A compound claimed in claim 9 wherein $R_5$, $R_6$, and $R_7$ are each independently hydrogen, chlorine, or methyl.

11. A compound as claimed in claim 10 and being 3-[2-[(2,6-dichloro-3-methylphenyl)amino]phenyl]-1,2,4-oxadiazol-5(4H)-one.

12. A pharmaceutical composition for use as an antiinflammatory agent comprising an antiinflammatory effective amount of a compound of claim 1 and a pharmacologically acceptable carrier.

13. A method of treating inflammation in a mammal suffering therefrom which comprises administering to said mammal a compound of claim 1 in unit dosage form.

* * * * *